United States Patent [19]
Griffiths

[11] Patent Number: 6,015,426
[45] Date of Patent: Jan. 18, 2000

[54] ROTATABLE LINKAGE FOR MICRO-INSTRUMENT

[75] Inventor: Jerry Richard Griffiths, Pembroke, Mass.

[73] Assignee: TNCO, Inc., Whitman, Mass.

[21] Appl. No.: 08/807,320

[22] Filed: Feb. 27, 1997

Related U.S. Application Data

[63] Continuation of application No. 08/274,642, Jul. 13, 1994, abandoned.

[51] Int. Cl.⁷ ...................................................... A61B 17/00

[52] U.S. Cl. ........................... 606/205; 128/751; 606/174

[58] Field of Search ................................ 606/1, 51, 52, 606/170, 174, 205, 211; 128/750–755; 604/22

[56] References Cited

U.S. PATENT DOCUMENTS 5,368,606  11/1994  Marlow et al. .......................... 606/174

FOREIGN PATENT DOCUMENTS 0165472  12/1985  European Pat. Off. ............... 606/208

*Primary Examiner*—William Lewis
*Attorney, Agent, or Firm*—Stephen Y. Chow; Perkins, Smith & Cohen, LLP; Timothy J. Shea, II

[57] ABSTRACT

A rotatable linkage for use in handling small objects at a distance, for example, in endoscopic surgery, by converting the longitudinal motion of a drive member to the opening and closing of jaws at the distal end of the drive member wherein the drive member is enclosed in an elongated housing on which the jaws are mounted which may be rotated relative to the drive member on a bearing by rotation of the housing.

20 Claims, 3 Drawing Sheets

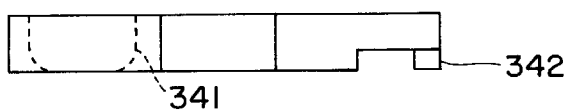
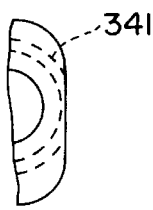
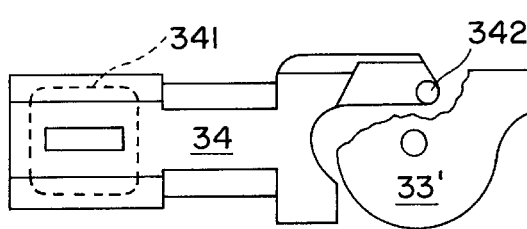
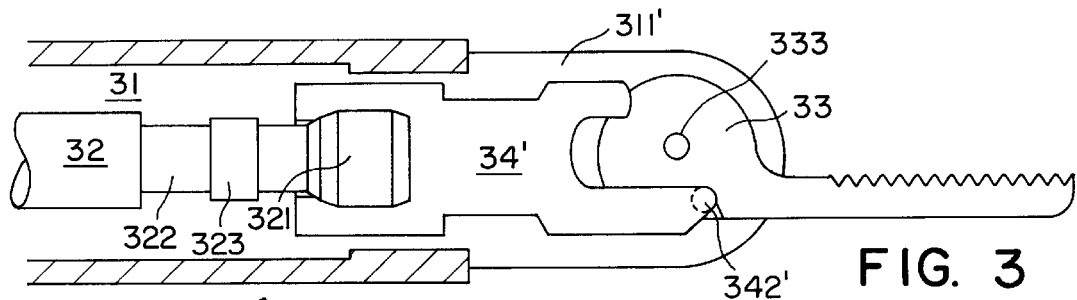
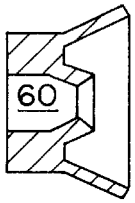
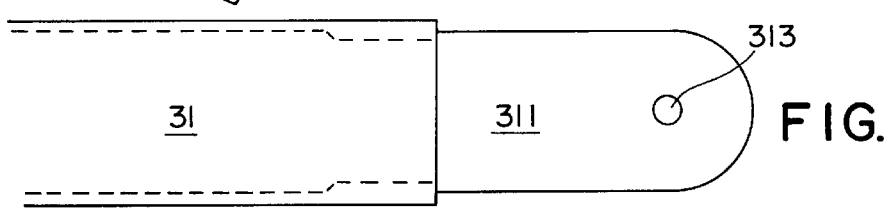
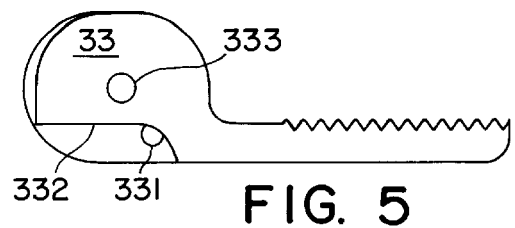

ROTATABLE LINKAGE FOR MICRO-INSTRUMENT

This application is a continuation of application Ser. No. 08/274,642 filed on Jul. 13, 1994, now abandoned.

BACKGROUND OF THE INVENTION

The field of the invention is that of micro-instrumentation, that is, articulating, hand-held, instruments used in micro-surgery, electronic micro-assembly and like applications, for grasping, cutting, punching out, probing and the like. The instruments can comprise scissor-handle actuators, so-called cigar handle linear or rotary activators, or other actuators, with push or pull force application design modes.

The invention is particularly advantageous for endoscopic, or minimally invasive, surgery, but is also advantageous in other applications for micro-instrumentation.

Prior art endoscopic devices have included the traditional scissor-like linkage shown in FIG. 1, in which a drive member 2, linked to the ends of a scissor-like configuration of jaws 3 and 4 on a pivot mounted at the distal end of a tube 1, is pulled to close the jaws. This traditional arrangement suffers from the disadvantage of using four pivots, typically pins, which are subjected to significant shearing force, particularly where the linkage portion is short compared to the jaws.

An improvement upon these traditional devices was disclosed in U.S. Pat. No. 5,152,790 to Honkanen et al. and U.S. Pat. No. 5,219,357 to Honkanen et al. One feature of those inventions is the use of one or two jaws rotatably mounted on a pivot, each jaw 23 with a recess 231 off center to accommodate and absorbs force from the distal end of an actuating link 24 minimize the width of the structure that pushes the jaw closed around the pivot. This relieves the shear force on a retaining pin 241 that positions the distal end of the actuating link and is used to rotate the jaw open. FIG. 2 hereto shows a two-jaw configuration (only one jaw shown) disclosed in the second mentioned Honkanen et al. patent where one linkage member is used for each jaw and a common drive shaft 22, terminating at its distal end in a "T" 221, by a one-quarter turn, engages channels 242 within the linkage members 24 to push or pull the linkage members to respectively close or open the jaws.

Although the disclosed device has advantages in strength and form factor over the traditional endoscopic tool, it did not fully meet some of the new demands of medical procedure, which include requirements of cleanliness.

SUMMARY OF THE INVENTION

It is a particular objective of the present invention to provide an endoscopic instrument that is rotatable at the jaws with little "play" between the parts to assure tactile sense by the user, for example, a surgeon.

It is another objective to provide an endoscopic instrument that can be sealed near the jaws to prevent the accumulation of biological debris within the instrument.

It is a further objective to provide an endoscopic instrument that allows flushing of the tip to prevent accumulation of biological debris.

The present invention comprises a rotatable linkage using a drive member with an end bearing with which a pair of actuating links are engaged and are fully rotatable about the longitudinal axis of the drive member. Each actuating link converts the lateral motion of the drive member to rotational motion of a jaw by pushing against the wall of a recess in the jaw, that jaw being mounted on a central pivot.

DESCRIPTION OF THE DRAWINGS

FIG. 3 is a cut-away view of the present invention showing one-half of the linkage.

FIG. 3A is a cut-away view of the second half of the linkage.

FIG. 3B is a view of the external tube with mounting for the linkage.

FIG. 4A is an end view of the actuating link shown in FIG. 3A.

FIG. 4B is a top view of the actuating link shown in FIG. 3A.

FIG. 5 is an unobstructed view of the jaw shown in FIG. 3.

FIG. 6 shows a seal used in the invention.

FIG. 6B shows an alternative seal used in the invention.

DETAILED DESCRIPTION

Figure 1:
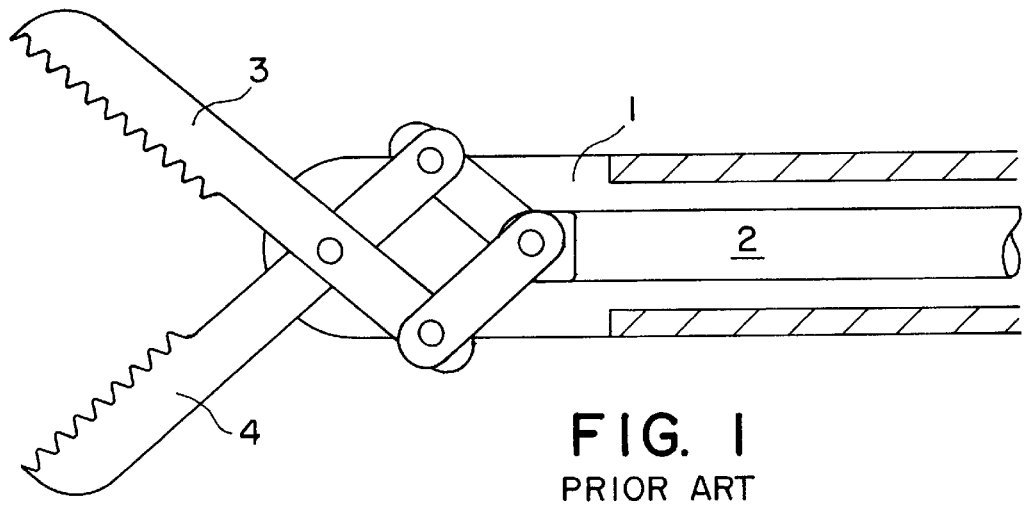
FIG. 1 is a cut-away view of a prior art micro-instrument.
Figure 2:
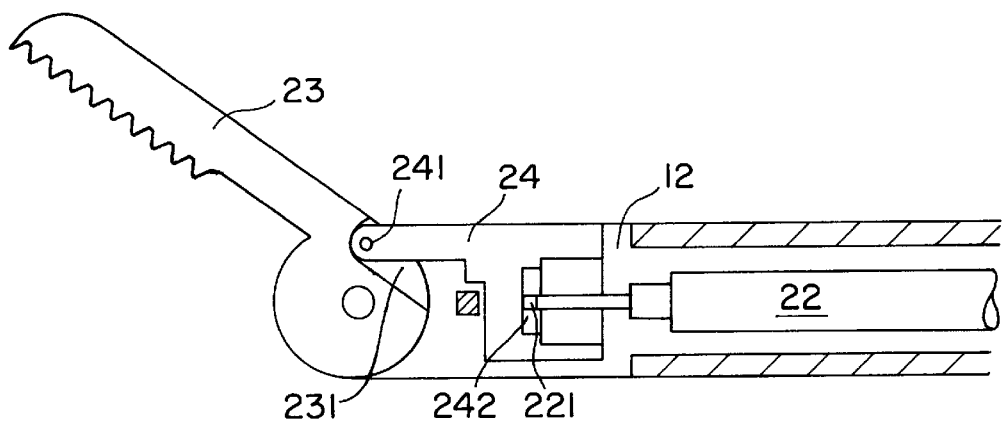
FIG. 2 is a cut-away view of another prior art micro-instrument.
Figure 7:
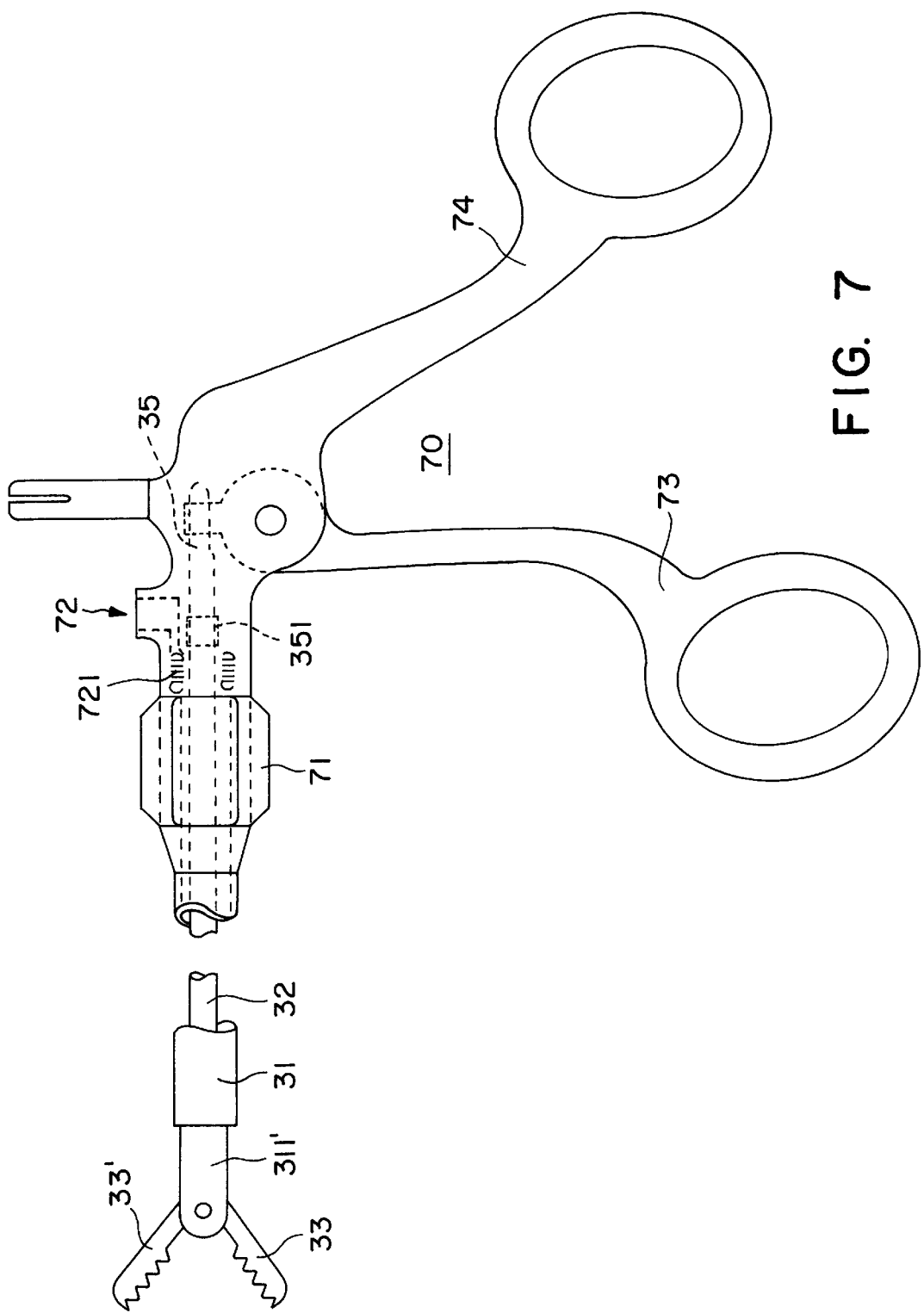
FIG. 7 shows the invention used in an endoscopic instrument.

FIG. 3 shows a cut-away view of the invention implemented in an endoscopic instrument in which 31 is a tube typically on the order of 12–18 inches long and 3–10 mm in diameter mounted in an instrument such as shown in FIG. 7 in which the end near the handles 73 and 74 is deemed the proximal end and the other end deemed the distal end.

Within tube or housing 31 is a drive element or shaft 32 which terminates at its distal end in a bearing 321 that is of barrel or cylindrical shape with a round distal end.

Referring to FIGS. 3 and 3A, actuating links 34 and 34' are assembled around bearing 321 of drive member 32 so that bearing 321 is set snugly within cavity 341 of actuating link 34, shown in FIGS. 3A, 4A and 4B, and a corresponding cavity in actuating link 34' not shown. In an assembled state within housing 31, the actuating links 34 and 34' may be reciprocated proximally and distally by drive element 32 and may move independently and slightly in pitch (rotating in the plane of FIG. 3).

Actuating links 34 and 34' are respectively coupled to jaws 33' and 33 shown in FIGS. 3, 3A and 5, to rotate the jaws around pivot 313, which may be a solid or hollow pin or shaft mounted on the distal end mount 311 (FIG. 3B) and 311' (FIG. 3). In the preferred embodiment, the actuating link, for example, link 34', is coupled to jaw 33 by a hub 342' (shown as nub 342 for link 34 in FIGS. 3A and 4B) positioned within a positioning hole 331 (FIG. 5) tangent to the distal ledge 332 of a recess. In this configuration, the distal movement of drive element 32 pushes the actuating links 34' and 34 forward, and the distal portions of the links at the respective nubs 342' and 342 push against the distal portion of ledge 332 and hole 331 and the corresponding elements of jaw 33' (not shown) to apply a moment force around pivot 313 and force the jaws 33' and 33 together for cutting or grasping purposes. The jaws are moved apart in this configuration by moving the drive element 32 proximally, applying an opposite moment force through the nubs 342' and 342. This configuration is particularly advantageous where the greater force is required upon the closing of the jaws, for example, for cutting, thus spreading the load across the entire distal portions of the actuating links. Other configurations may be used for spreading the load on the retraction cycle.

The slight pitch allowance for the actuating links 34' and 34 allows their distal portions to follow the ledge 332 and corresponding element in jaw 33', but to maintain a snug feel for the operator, such as an endoscopic surgeon. This feel is enhanced by allowing the rotational joint to be placed at the distal end 321 of the fixed drive shaft rather than at the proximal end of the instrument as in known devices, which result in more rotational play. Thus, in FIG. 7, the proximal end 35 of the drive element 32 is rotationally fixed, while housing 31 is rotated using knob 71. Handles 73 and 74 are linked to reciprocate the drive element 32 distally or proximally.

Optionally, and as part of the advantage of the present invention, a detente 322 and abutment 323 may be provided on the drive element 32 to accommodate unidirectional resilient seal 60 shown in FIG. 6 so that debris from cutting or punching and other fluids are prevented from traveling proximally from the distal end of the instrument past the seal, and the entire instrument may be flushed from the proximal end, for example, using flushport 72 in FIG. 7, towards the distal end, which allows unidirectional insertion of fluid through check-valve 721 (a proximal seal is shown at 351). The unique linkage of the invention facilitates assembly by stretching seal 60 over the bearing 321 and placing seal 60 at a maximally distal portion of the instrument at 322. Other seals, such as two-way seals, such as O-ring 60' shown in FIG. 6B, may be used.

What is claimed is:

1. A miniature articulated tip tool assembly comprising:
    (a) an elongated housing defining a channel therein and having at a distal end thereof a pivotal mounting for at least one jaw member;
    (b) an elongated drive member positioned within said channel terminating at its distal end in a bearing characterized in being (i) rotationally symmetric about the longitudinal axis of said drive member, (ii) round in longitudinal cross section at its distal end, and (iii) greater in diameter at its widest radial cross section than at its proximal end;
    (c) at least one single-piece actuating link defining a seat for engaging said bearing and a surface for transmitting force parallel to the longitudinal axis of said drive member, but separated therefrom by a radial moment arm, said link engaging at said seat said bearing allowing, between said link and said bearing, (i) full rotation about the longitudinal axis, (ii) limited rotation in the plane of said moment arm; and (iii) substantially no other relative motion; and
    (d) at least one jaw member mounted for rotation on said pivotal mounting and engaging, at a point separated from said pivotal mounting as projected upon the plane of said jaw rotation, said force-transmitting surface of said link.

2. The apparatus of claim 1 further comprising a seal between said housing and said drive member distally positioned to substantially abut the most proximal position of the link member.

3. The apparatus of claim 2 wherein the seal is an O-ring.

4. The apparatus of claim 1 further comprising a stop-valve allowing unidirectional fluid flow positioned to substantially abut the most proximal position of the link member.

5. The apparatus of claim 4 wherein the stop-valve is an annular skirt composed of resilient material.

6. A miniature articulated tip tool assembly comprising:
    (a) an elongated housing defining a channel therein and having at a distal end thereof pivotal mounting for at least one jaw member;
    (b) an elongated drive member positioned within said channel terminating at its distal end in a substantially cylindrical bearing with a round distal end and co-axial with the longitudinal axis of said drive member;
    (c) at least one single-piece actuating link defining a seat substantially complementary to a segment of said bearing for closely engaging said bearing and a surface for transmitting force parallel to the longitudinal axis of said drive member, but separated therefrom by a radial moment arm; and
    (d) at least one jaw member mounted for rotation on said pivotal mounting and engaging, at a point separated from said pivotal mounting as projected upon the plane of said jaw rotation, said force-transmitting surface of said link.

7. The apparatus of claim 6 further comprising a seal between said housing and said drive member distally positioned to substantially abut the most proximal position of the link member.

8. The apparatus of claim 7 wherein the seal is an O-ring.

9. The apparatus of claim 6 further comprising a stop-valve allowing unidirectional fluid flow positioned to substantially abut the most proximal position of the link member.

10. The apparatus of claim 9 wherein the stop-valve is an annular skirt composed of resilient material.

11. A miniature articulated tip tool assembly comprising:
    (a) an elongated housing defining a channel therein and having at a distal end thereof pivotal mounting for a pair of opposing jaws;
    (b) an elongated drive member positioned within said channel terminating at its distal end in a substantially cylindrical bearing with a round distal end and coaxial with the longitudinal axis of said drive member;
    (c) a pair of single-piece actuating links each defining a seat substantially complementary to a segment of said bearing for closely engaging said bearing and a surface for transmitting force parallel to the longitudinal axis of said drive member, but separated therefrom by a radial moment arm; and
    (d) a pair of jaws each mounted for rotation on said pivotal mounting and engaging, at a point separated from said pivotal mounting as projected upon the plane of said jaw rotation, said force-transmitting surface of said link.

12. The apparatus of claim 11 further comprising a seal between said housing and said drive member distally positioned to substantially abut the most proximal position of the link member.

13. The apparatus of claim 12 wherein the seal is an O-ring.

14. The apparatus of claim 11 further comprising a stop-valve allowing unidirectional fluid flow positioned to substantially abut the most proximal position of the link member.

15. The apparatus of claim 14 wherein the stop-valve is an annular skirt composed of resilient material.

16. The apparatus of claim 11 wherein the force-transmitting surface is at the distal end of said actuating link.

17. The apparatus of claim 16 further comprising a seal between said housing and said drive member distally positioned to substantially abut the most proximal position of the link member.

18. The apparatus of claim 17 wherein the seal is an O-ring.

19. The apparatus of claim 16 further comprising a stop-valve allowing unidirectional fluid flow positioned to substantially abut the most proximal position of the link member.

20. The apparatus of claim 19 wherein the stop-valve is an annular skirt composed of resilient material.

* * * * *